United States Patent [19]

Kitahara et al.

[11] Patent Number: 4,654,435

[45] Date of Patent: Mar. 31, 1987

[54] PROCESS FOR ADDITION REACTION OF UNSATURATED ORGANIC COMPOUNDS

[75] Inventors: Shizuo Kitahara, Kawaguchi; Yoshitsugu Hirokawa, Yokohama; Haruki Kawada, Yokohama; Toshihiro Fujii, Yokohama; Nagatoshi Sugi, Yokohama; Hiroaki Hasegawa, Yokohama; Akira Yoshioka, Kamakura, all of Japan

[73] Assignee: Nippon Zeon Co., Ltd., Tokyo, Japan

[21] Appl. No.: 563,379

[22] Filed: Dec. 20, 1983

[30] Foreign Application Priority Data

Dec. 25, 1982 [JP] Japan ............................. 57-234558

[51] Int. Cl.$^4$ ............................................. C07C 69/76
[52] U.S. Cl. ...................................... 560/61; 560/51; 562/459; 562/464; 562/471
[58] Field of Search .................... 560/61, 51; 562/471, 562/459, 464

[56] References Cited

U.S. PATENT DOCUMENTS 3,280,170 10/1966 Miller .................................... 560/61
4,435,590 3/1984 Shalaby ................................. 560/61

FOREIGN PATENT DOCUMENTS

EP40177 11/1981 European Pat. Off. ............ 560/181

Primary Examiner—Paul J. Killos
Attorney, Agent, or Firm—Sherman and Shalloway

[57] ABSTRACT

A process for the addition reaction of an unsaturated organic compound, except a rubber, having at least one carbon-carbon double bond in a molecule, which comprises reacting the unsaturated organic compound with an organic compound having a carboxyl group and an aldehyde group in the presence of a Lewis acid.

14 Claims, No Drawings

PROCESS FOR ADDITION REACTION OF UNSATURATED ORGANIC COMPOUNDS

This invention relates to a process wherein industrially useful compounds are obtained by conducting rapidly efficiently the addition reaction between unsaturated organic compounds (hereinafter referred to as "unsaturated compounds"), except rubbers, having a carbon-carbon double bond and organic compounds having both a carboxyl group and an aldehyde group.

Methods (Prince reaction, etc.) of reacting unsaturated compounds with carboxylic acids or aldehydes in the presence of acid catalysts have been hitherto widely known.

This invention is based on a new finding that compounds having both a carboxyl group and an aldehyde group allow the distinct addition reaction with unsaturated compounds in the presence of acid catalysts, i.e., they are reacted with the organic compounds rapidly at low temperatures in good efficiency compared to compounds having only one of the carboxyl group and the aldehyde group. The process of this invention has such advantages that a rate of reaction is high, an efficiency of addition is high and side reactions such as a crosslinking reaction, etc. are little involved.

The unsaturated compounds used in this invention are unsaturated organic compounds, except rubbers, having at least one carbon-carbon double bond (C=C) in a molecule. More specifically, said compounds are resinous polymers having at least one carbon-carbon double bond in a molecule and organic compounds, other than resinous polymers, selected from compounds having at least one carbon-carbon double bond in a molecule and a molecular weight of not more than 50,000. Preferable examples thereof are liquid polymers, oligomers and low molecular weight compounds such as a monoolefin and a diolefin. Among said unsaturated compounds, those having in the molecule a structure of formula

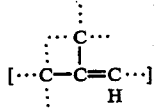

[I]

or a structure of formula

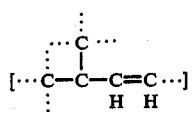

[II]

wherein each dotted portion represents a covalent bond with hydrogen, carbon or other atoms and may form part of a ring, are most preferable as they have a high rate of addition reaction.

Examples of the compound having the structure of formula [I] include 2-methyl-2-butene, 1-methylcyclohexene, α-methylstyrene, an isoprene homopolymer except a rubber, an isoprene copolymer except a rubber, squalene and chicle. Examples of the compound having the structure of formula [II] include 4-methyl-2-pentene, dicyclopentadiene, a 1,3-pentadiene homopolymer except a rubber, a 1,3-pentadiene copolymer except a rubber, an ethylidene norbornene homopolymer, an ethylidene norbornene copolymer, a dicyclopentadiene homopolymer and a dicyclopentadiene copolymer. Examples of the unsaturated compounds having no structure of formula [I] or [II] include 1- or 2-butene, 1-, 2-, 3- or 4-octene, cyclohexene, a butadiene homopolymer except a rubber and a butadiene copolymer except a rubber.

The organic compound containing a carboxyl group and an aldehyde group used in this invention is a compound containing at least one carboxyl group and at least one aldehyde group. Examples of the organic compound include linear aliphatic compounds having up to about 20 carbon atoms, aromatic compounds having a benzene ring, a naphthalene ring, a pyridine ring or a furane ring, and alicyclic compounds having a cyclopentane ring, a cyclopentene ring or a cyclohexane ring. These compounds may contain an oxygen atom, a sulfur atom, a nitrogen atom or a multiple bond in molecular chains. Moreover, the hydrogen atom in the molecule may be substituted by a halogen atom, an alkyl group, an alkoxy group, an acyl group, a hydroxyl group, a nitrile group, an amino group, etc. if the substitution does not adversely affect the reaction.

More specifically, the aliphatic compounds having a carboxyl and an aldehyde group include glyoxylic acid, formylacetic acid, 2-formylacrylic acid, 6-formylhexanoic acid, 8-formyloctanoic acid, formylmethoxyacetic acid, 2-formylethylacetic acid, and 3-(carbomethoxy)propionaldehyde. The aromatic compounds include 2-, 3- or 4-carboxybenzaldehyde, 2-formyl-5-acetyl-benzoic acid, 2-, 3- or 4-formylphenylacetic acid, 2-formyl-5-hydroxyphenylacetic acid, 3-(2-formylphenyl)-propionic acid, 2-formylcinnamic acid, 1,8-naphthaldehyde acid, 2-, 3- or 4-formylphenoxyacetic acid, 2-formyl-4-methylphenoxyacetic acid, 2-(2-formylphenoxy)propionic acid, 3-(2-formylphenoxy)propionic acid, 2-formyl-1-phenoxyisovaleric acid, 6-(2-, 3- or 4-formylphenoxy)-hexanoic acid, (2-formylphenyl)-methoxyacetic acid, 2-, 3- or 4-formylphenylthioacetic acid, (1-formyl-2-naphthyloxy)acetic acid, [(5-formyl-2-furyl)thio]acetic acid, (8-formyl-2-oxo-2H-1-benzopyran-7-yl-oxy)acetic acid, 2-, 3- or 4-carboxyphenoxyacetaldehyde, and 2-(formylmethoxy)phenoxyacetic acid. The alicyclic compounds include 2-formylcyclopentanecarboxylic acid, 4-formyl-2-cyclopentenecarboxylic acid and 2-formylcyclohexanecarboxylic acid.

Among these organic compounds, those having such a structure that the carboxyl group and the aldehyde group are easy of three-dimensionally or thermodynamically approaching each other moderately in the molecule through an acid catalyst, particularly compounds having an aromatic ring in which the carboxyl group or an atomic grouping containing this group and the aldehyde group or an atomic grouping containing this group are located adjacent to each other on the ring (at the ortho-position when the ring is a benzene ring), are especially preferred in this invention because they lead to a high rate of reaction.

When 2-formylphenoxyacetic acid, 3-(2-formylphenoxy)propionic acid, etc., which are compounds exhibiting a high rate of addition reaction with the unsaturated compounds, are mixed with tin tetrachloride, the formation of a red color (having a visible light absorption at approximately 510 nm) presumably owing to the coordination of the carbonyl group with tin tetrachloride is observed. Infrared absorption spectrum test leads to the observation that the C=O stretching vibration of the aldehyde group and the carboxyl group is shifted to a lower wavelength owing to the presence of tin tetrachloride. From these facts, it is presumed that in the process of this invention, the rate of addition reaction is increased by the coordination of a tin tetrachloride catalyst with both of the carboxyl group and the aldehyde group.

The amount of the organic compound having a carboxyl and an aldehyde group is not particularly restricted but properly selected depending on a purpose. Usually, it is 0.0001 to 2 moles per mole equivalent of the carbon-carbon double bond of the unsaturated compound.

Typical examples of the Lewis acids used in this invention are halides of metals or semi-metals, for example, halogen compounds or organic halogen compounds of elements such as Be, B, Al, Si, P, S, Ti, V, Fe, Zn, Ga, Ge, As, Se, Zr, Nb, Mo, Cd, Sn, Sb, Te, Ta, W, Hg, Bi and U or oxygen-element combinations such as PO, SeO, SO, $SO_2$ or VO, and complexes of these. Preferred acid catalysts are those which form a coordination bond with the organic compounds having a carboxyl and an aldehyde group. Especially preferred are those acid catalysts whose coordination products with the organic compounds have an orange color (absorption wavelength 480 nm) or a deeper color. Specific examples include $BF_3$, $(CH_3)_2BF$, $BCl_3$, $AlCl_3$, $AlBr_3$, $(C_2H_5)AlCl_2$, $POCl_3$, $TiCl_4$, $VCl_4$, $MoCl_5$, $SnCl_4$, $(CH_3)SnCl_3$, $SbCl_5$, $TeCl_4$, $TeBr_4$ and $WCl_6$. Of these, $SnCl_4$, $BCl_3$, $WCl_6$ and $SbCl_5$ are especially suitable because they lead to a high rate of reaction and cause little side reactions. It is of course possible to use two or more of the Lewis acids. The amount of the Lewis acid catalyst is not particularly limited. Usually, it is 0.01 to 5 moles, preferably 0.05 to 2 moles, per mole of the organic compound having a carboxyl and an aldehyde group.

The reaction in this invention is usually performed in the presence of a suitable solvent. Or it is advantageously carried out in solution in the absence of a solvent. Preferable examples of the solvent include aromatic solvents such as benzene and toluene, paraffinic solvents such as butane and hexane and halogenated hydrocarbon solvents such as chloroform and dichloroethane. Suitable solvents are those which are inert to the acid catalyst, etc. and dissolve the unsaturated compounds. Solvents which have some extent of solubility in the organic compound having a carboxyl and an aldehyde group or the acid catalyst are especially appropriate from the aspect of a rate of reaction, etc. However, those solvents are not altogether critical.

The organic compound having a carboxyl and an aldehyde group and the acid catalyst may be separately added to the reaction system, or after they are mixed in advance (in which case a chemical change may occur). All of the Lewis acid may be added in the initial stage of the reaction, or it may be added portionwise or continuously during the reaction. In order to maintain the activity of the catalyst and prevent side reactions, it is advisable to keep the reaction system in an anhydrous state or at a limited water content. Further, the presence of oxygen is usually not desirous.

The reaction temperature is not limited in particular. Usually, it is −20° C. to 200° C., preferably 0° to 100° C. The reaction time is properly set in the range of 10 seconds to 50 hours. The reaction can cease upon adding water, alcohols or alkali solutions of these. After reaction, removal of a catalyst residue, an unreacted substance, etc. and separation and purification can be conducted if required by optional procedures such as water-washing, extraction, etc. to obtain final products.

Since the process of this invention can provide addition reaction products containing large amounts of components having a carboxyl group, it is utilizable for synthesis of carboxyl group-containing compounds such as starting materials for emulsifying agents. Said process is also available in the field of adhesives and coatings by applying it to oligomers or polymers.

The following Examples illustrate this invention more specifically.

EXAMPLE 1

Two grams of liquid polyisoprene having a molecular weight of about 25,000 and a cis-1,4 linkage content of 86% was dissolved in 25 ml of dehydrated benzene. While stirring with a magnetic stirrer, each of organic compounds indicated in Table 1 was added to the solution at 25° C. in a conical flask under an atmosphere of nitrogen. Subsequently, each of acid catalysts indicated in Table 1 was added dropwise as a benzene solution. Stirring continued for a reaction time indicated in Table 1, and about 3 ml of methyl alcohol was added to cease the reaction. The reaction liquid was washed with water in a separating funnel to remove an unreacted substance. Ten milligrams of 2,6-ditertiary butyl-4-methylphenol as an antioxidant was then added. After the major proportion of benzene was removed by evaporation, vacuum drying was conducted. There resulted samples A–H.

The amount of the organic compound introduced in each of these samples as shown in Table 1 was determined through gel permination chromatography with an ultraviolet absorption spectrometer by making use of absorption at a wavelength of 275 nm of the aromatic ring incorporated in polyisoprene. The carboxyl group introduced in polyisoprene was quantitatively determined by a neutralization titration method. The results are shown in Table 1.

TABLE 1

| Sample | Organic compound (g) | Acid catalyst (g) | Reaction time (min.) | Amount introduced into polyisoprene (mole/100 g) Organic compound | Amount introduced into polyisoprene (mole/100 g) Carboxyl group | Color of a solution during reaction |
|---|---|---|---|---|---|---|
| A* | — | $SnCl_4$ (0.015) | 30 | — | below 0.0002 | Colorless |
| B* | Benzoic acid (0.02) | $SnCl_4$ (0.0015) | 30 | below 0.0002 | below 0.0002 | Pale yellow |
| C* | Benzaldehyde (0.02) | $SnCl_4$ (0.0015) | 30 | below 0.0002 | — | Pale yellow |
| D | 2-Formylphenoxyacetic acid (0.021) | $SnCl_4$ (0.015) | 30 | 0.0026 | 0.0015 | Red |

TABLE 1-continued

| Sample | Organic compound (g) | Acid catalyst (g) | Reaction time (min.) | Amount introduced into polyisoprene (mole/100 g) Organic compound | Amount introduced into polyisoprene (mole/100 g) Carboxyl group | Color of a solution during reaction |
|---|---|---|---|---|---|---|
| E | 3-(2-Formylphenoxy)-propionic acid (0.021) | SnCl$_4$ (0.015) | 30 | 0.0022 | 0.0010 | Red |
| F | 2-Carboxybenzaldehyde (0.018) | BCl$_3$ (0.007) | 60 | 0.0016 | 0.0009 | Whitish red |
| G | 2-Formylphenoxyacetic acid (0.021) | WCl$_6$ (0.024) | 60 | 0.0012 | 0.0006 | Reddish Violet |
| H | 3-(2-Formylphenyl)-propionic acid (0.021) | SnCl$_4$ (0.015) | 20 | 0.0013 | 0.0010 | Red |

*Comparative samples

EXAMPLE 2

Two grams each of unsaturated compounds indicated in Table 2 was dissolved in 25 ml of dehydrated benzene. While stirring with a magnetic stirrer, 2-formylphenoxyacetic acid in an amount indicated in Table 2 was added to the solution at 25° C. in a conical flask under an atmosphere of nitrogen. Thereafter, tin tetrachloride in an amount indicated in Table 2 was added dropwise, and stirring further continued for a reaction time indicated in Table 2. About 3 ml of methyl alcohol was added and the reaction ceased. The reaction liquid was washed with water in a separating funnel to remove an unreacted substance. After the major proportion of benzene was removed by evaporation, vacuum drying was carried out. Samples I-L were thus obtained.

The amount of 2-formylphenoxyacetic acid introduced in each of these samples was determined through gel permeation chromatography with an ultraviolet absorption spectrometer by making use of absorption at a wavelength of 275 nm of the aromatic ring incorporated. The carboxyl group introduced in the unsaturated compound was quantitatively determined through gel permeation chromatography with an infrared absorption spectrometer. The results are indicated in Table 2.

of an aqueous solution of dilute sodium hydroxide was added and the reaction stopped (pH about 12). Ether extraction was repeated in a separating funnel to separate the reaction mixture into an aqueous phase and an ether phase.

Hydrochloric acid was added to the aqueous phase to adjust the pH to about 2. The components extracted with ether were collected through gel permeation chromatography and esterified with diazomethane. The treated components were separated and purified upon column chromatography and vacuum distillation. Analysis of the infrared absorption spectrum for each of the components revealed that absorption of an ester group was observed at approximately 1735 cm$^{-1}$. This showed that the components in the aqueous phase were all compounds having a carboxyl group. Moreover, analysis of $^1$H-NMR spectrum, $^{13}$C-NMR spectrum, mass spectrum and infrared absorption spectrum indicated that the mixture contained, besides unreacted 2-formylphenoxyacetic acid, a compound presumed to have a structure of formula:

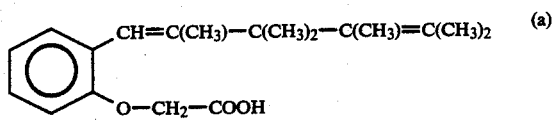
(a)

TABLE 2

| Sample | Unsaturated compound | 2-Formyl-phenoxy-acetic acid (g) | SnCl$_4$ (g) | Reaction time (min.) | Amount introduced into the unsaturated compound (mole/100 g) 2-Formylphenoxy-acetic acid | Amount introduced into the unsaturated compound (mole/100 g) Carboxyl group |
|---|---|---|---|---|---|---|
| I | Petroleum resin (A)[1] | 0.18 | 0.26 | 120 | 0.031 | 0.010 |
| J | Petroleum resin (B)[2] | 0.18 | 0.26 | 120 | 0.038 | 0.016 |
| K | Squalene[3] | 0.36 | 0.52 | 30 | 0.072 | 0.031 |
| L | Guttapercha[4] | 0.021 | 0.015 | 30 | 0.003 | 0.007 |

Notes:
[1]Petroleum resin having a molecular weight of about 2,000 and obtained by subjecting a mixture of 1,3-pentadiene, cyclopentene and butene (their weight ratio is about 65/14/21) to cation polymerization with a Friedel-Crafts catalyst.
[2]Petroleum resin having a molecular weight of about 1,000 and obtained by heat-polymerizing dicyclopentadiene.
[3]Compound having a structure of formula:

[4]Natural resinous polymer composed mainly of trans-polyisoprene.

EXAMPLE 3

Hundred milliliters of dehydrated benzene was added to 5 g of 2-methyl-2-butene. While stirring with a magnetic stirrer, 1 g of 2-formylphenoxyacetic acid was added to the solution at 25° C. in a conical flask under an atmosphere of nitrogen. Subsequently, 0.5 g of tin tetrachloride was added dropwise as a benzene solution, and stirring further continued at 25° C. for 4 hours. The color of the reaction liquid was red. Thereafter, 200 ml and a compound presumed to have a structure of formula:

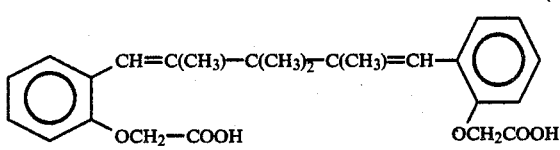

A mixture recovered from the ether phase was separated and purified by column chromatography (silica gel) and vacuum distillation. Analysis was conducted as above and absorption of an ester group was ascertained. It was further confirmed that the mixture contained a compound presumed to have a structure of formula:

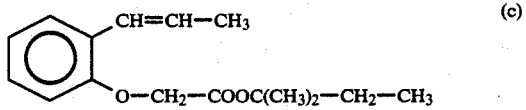

and a compound presumed to have a structure of formula:

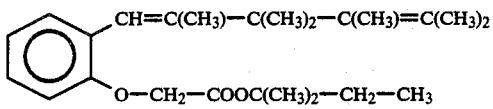

Of the overall recovered product after reaction, about 25% was the compound of formula (a), about 15% was the compound of formula (b), about 26% was the compound of formula (c), about 14% was the compound of formula (d) and about 20% was unreacted 2-formylphenoxyacetic acid and a compound whose structure was unconfirmed.

EXAMPLE 4

The procedure of Example 3 was followed except that 2-methyl-2-butene was replaced with 1-methylcyclohexene. It was ascertained that at least three types of compounds having a carboxyl group, except the starting 2-formylphenoxyacetic acid, were contained in an aqueous phase and at least one component having an ester group was contained in an ether phase. A rate of consumption (rate of reaction) of 2-formylphenoxyacetic acid was about 80%.

EXAMPLE 5

The procedure of Example 3 was repeated except that 2-methyl-2-butene was replaced with α-methylstyrene. It was confirmed that at least one component having a carboxyl group, except the starting 2-formylphenoxyacetic acid, was contained in an aqueous phase and at least one component having an ester group was contained in an ether phase. A rate of consumption (rate of reaction) of 2-formylphenoxyacetic acid was about 90%.

EXAMPLE 6

The procedure of Example 3 was repeated except that 2-methyl-2-butene was replaced with cyclohexene. It was confirmed that at least one component having a carboxyl group, except the starting 2-formylphenoxyacetic acid, was contained in an aqueous phase and at least three components having an ester group were contained in an ether phase. A rate of consumption (rate of reaction) of 2-formylphenoxyacetic acid was about 20%.

What is claimed is:

1. A process for the addition reaction of a nonrubbery unsaturated organic compound having at least one carbon-carbon double bond in its molecule, wherein the compound is selected from the group consisting of 2-methyl-2-butene, 1-methylcyclohexene, alpha-methyl styrene, an isoprene homopolymer, an isoprene copolymer, squalene, chicle, 4-methyl-2-pentene, dicyclopentadiene, 1,3-pentadiene homopolymer, 1,3-pentene, copolymer, an ethylidene norbornene homopolymer, an ethylidene norbornene copolymer, a dicyclopentadiene homopolymer, a dicyclopentadiene copolymer, 1- or 2-butene, 1-, 2-, 3-, or 4-octene, cyclohexene, a butadiene homopolymer and a butadiene copolymer, which comprises reacting (A) the unsaturated organic compound with (B) an aromatic compound having a benzene ring, a naphthalene ring, a pyridene ring or a furan ring; a linear aliphatic compound having up to about 20 carbon atoms; or an alicyclic organic compound having a cyclopentane, cyclopentene, or cyclohexane ring, and having a carboxyl group and an aldehyde group, in the presence of a Lewis acid and a solvent, at a temperature of 0° to 100° C., said compound (B) having the carboxyl group and aldehyde group being used in an amount of 0.0001 to 2 moles per mole of the compound (A) and said Lewis acid being used in an amount of 0.01 to 5 moles per mole of the compound (B).

2. The process of claim 1 wherein the unsaturated organic compound is a compound having in a molecule a structure of formula

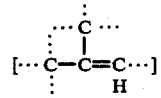

wherein each dotted portion represents a covalent bond with hydrogen, carbon or other atoms and may form part of a ring.

3. The process of claim 2 wherein the compound having the structure of formula [I] is a compound selected from the group consisting of 2-methyl-2-butene, 1-methylcyclohexene, α-methylstyrene, an isoprene homopolymer, an isoprene copolymer, squalene and chicle.

4. The process of claim 1 wherein the unsaturated organic compound is a compound having in a molecule a structure of formula

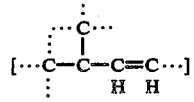

wherein each dotted portion represents a covalent bond with hydrogen, carbon or other atoms and may form part of a ring.

5. The process of claim 4 wherein the compound having the structure of formula [II] is a compound selected from the group consisting of 4-methyl-2-pentene, dicyclopentadiene, a 1,3-pentadiene homopolymer, a 1,3-pentadiene copolymer, an ethylidene norbornene homopolymer, an ethylidene norbornene copolymer, a dicyclopentadiene homopolymer and a dicyclopentadiene copolymer.

6. The process of claim 1 wherein the unsaturated organic compound is a compound selected from the group consisting of 1- or 2-butene, 1-, 2-, 3- or 4-octene, cyclohexene, a butadiene homopolymer and a butadiene copolymer.

7. The process of claim 1 wherein the organic compound having a carboxyl group and an aldehyde group is an aromatic compound.

8. The process of claim 1 wherein the organic compound having a carboxyl group and an aldehyde group is an organic compound having an aromatic ring in which the carboxyl group or an atomic grouping containing this group and the aldehyde group or an atomic grouping containing this group are located adjacent to each other on the aromatic ring.

9. The process of claim 1 wherein the organic compound having a carboxyl group and an aldehyde group is 2-formylphenoxyacetic acid, 3-(2-formylphenoxy)-propionic acid, 3-(2-formylphenyl)propionic acid or 2-carboxybenzaldehyde.

10. The process of claim 1 wherein the organic compound having a carboxyl group and an aldehyde group is an aliphatic compound.

11. The process of claim 1 wherein the organic compound having a carboxyl group and an aldehyde group is an alicyclic compound.

12. The process of claim 1 wherein the Lewis acid is a halide of a metal or semi-metal.

13. The process of claim 1 wherein the Lewis acid is a chloride of tin, boron, tungsten or antimony.

14. The process of claim 1 wherein the organic compound having a carboxyl and an aldehyde group is selected from the group consisting of glyoxylic acid, formylacetic acid, 2-formylacrylic acid, 6-formylhexanoic acid, 8-formyloctanoic acid, formylmethoxyacetic acid, 2-formylethylacetic acid, 3-(carbomethoxy)-propionaldehyde, 2-, 3-, or 4-carboxybenzaldehyde, 2-formyl-5-acetyl-benzoic acid, 2-, 3-, or 4-formylphenylacetic acid, 2-formyl-5-hydroxyphenylacetic acid, 3-(2-formylphenyl)propionic acid, 2-formylcinnamic acid, 1,8-naphthaldehyde acid, 2-, 3-, or 4-formylacetic acid, 2-formyl-4-methylphenoxyacetic acid, 2-(2-formylphenoxy)propionic acid, 3-(2-formylphenoxy)propionic acid, 2-formyl-1-phenoxyisovaleric acid, 6-(2-, 3- or 4-formylphenoxy)-hexanoic acid, (2-formylphenyl)methoxyacetic acid, 2-, 3- or 4-formylphenylthioacetic acid. (1-formyl-2-naphthyloxy)acetic acid, ((5-formyl-2-furyl)thio)acetic acid, (8-formyl-2-oxo-2H-1-benzopyran-7-yl-oxy)acetic acid, 2-, 3- or 4-carboxyphenylacetaldehyde, 2-(formylmethoxy)-phenoxyacetic acid, 2-formylcyclopentanecarboxylic acid, 4-formyl-2-cyclopentenecarboxylic acid and 2-formylcyclohexanecarboxylic acid; said organic compound having a carboxyl group and an aldehyde group being used in an amount of 0.0001 to 2 moles per mole of the carbon-carbon double bond of the unsaturated organic acid and the Lewis acid being used in an amount of 0.01 to 5 moles per mole of the organic compound having a carboxyl group and an aldehyde group.

* * * * *

UNITED STATES PATENT AND TRADEMARK OFFICE
CERTIFICATE OF CORRECTION

PATENT NO. : 4,654,435
DATED : March 31, 1987
INVENTOR(S) : KITAHARA, ET AL.

It is certified that error appears in the above-identified patent and that said Letters Patent is hereby corrected as shown below:

Column 8, line 11, claim 1, delete "1,3-pentene", insert --1,3-pentadiene--.

Signed and Sealed this

Twenty-sixth Day of January, 1988

*Attest:*

DONALD J. QUIGG

*Attesting Officer*    *Commissioner of Patents and Trademarks*